United States Patent [19]
Jem et al.

[11] Patent Number: 5,654,197
[45] Date of Patent: Aug. 5, 1997

[54] METHOD AND APPARATUS FOR GROWING BIOMASS PARTICLES

[75] Inventors: Kwan-Min Jem, Malvern, Pa.; Pierre-Francois Cevey, Crisser, Switzerland

[73] Assignee: Applied Research Systems ARS Holding N.V., Curacao, Netherlands Antilles

[21] Appl. No.: 102,098

[22] Filed: Aug. 6, 1993

Related U.S. Application Data

[63] Continuation-in-part of Ser. No. 822,301, Jan. 17, 1992, abandoned.

[51] Int. Cl.$^6$ .............................. C12N 5/02; C12M 3/02
[52] U.S. Cl. .................. 435/383; 435/403; 435/261; 435/297.2; 435/308.1
[58] Field of Search .................. 435/240.1, 240.22, 435/240.23, 240.24, 240.25, 240.46, 243, 261, 284–286, 311, 313, 315, 316, 813; 210/800, 513, 616, 538, 540, 150, 151, 615; 422/101, 225, 228, 269, 271

[56] References Cited

U.S. PATENT DOCUMENTS

| | | | |
|---|---|---|---|
| 4,335,215 | 6/1982 | Tolbert et al. | 435/286 |
| 4,814,278 | 3/1989 | Hamamoto et al. | 435/286 |

FOREIGN PATENT DOCUMENTS

| | | | |
|---|---|---|---|
| 8057037 | 11/1988 | Japan | 435/286 |
| 1095769 | 4/1989 | Japan | 435/286 |
| 3080077 | 4/1991 | Japan | 435/284 |
| 9106627 | 5/1991 | WIPO | 435/286 |

OTHER PUBLICATIONS

Tokashiki et al. "High Density Culture of Mouse–Human Hybridoma Cells Using a New Perfusion Culture Vessel" (Mar. 14, 1988) pp. 337–341.

Tolbert et al., "Manufacture of Pharmacologically Active Proteins by Mammalian Cell Culture" *Biopharm Mfg.*, Sep. 1987.

Feder et al., "The Large–Scale Cultivation of Mammalian Cells", *Scientific American*. vol. 248, No. 36 (Jan. 1983) pp. 36–43.

*Primary Examiner*—Paula K. Hutzel
*Attorney, Agent, or Firm*—Browdy and Neimark

[57] ABSTRACT

The present invention provides an improved method and apparatus for growing biomass particles, particularly microcarrier-bound cells, in an agitated suspension culture vessel in which fresh culture medium is added and spent culture medium is withdrawn continuously or semi-continuously. The improvement comprises withdrawing the spent culture medium through a particle settling chamber located within the vessel and at least partially immersed in the agitated culture medium therewithin. The particle settling chamber comprises a hollow container with a bottom opening through which biomass particles, such as microcarrier-bound cells, settle by gravity back into the agitated culture medium and a top opening through which particle-free spent culture medium is withdrawn form the vessel. The settling chamber is configured such that the fluid velocity of culture medium entering the settling chamber through the bottom opening is significantly less than the biomass particle settling velocity.

15 Claims, 5 Drawing Sheets

METHOD AND APPARATUS FOR GROWING BIOMASS PARTICLES

This application is a continuation in part of U.S. Ser. No. 07/822,301, filed Jan. 17, 1992, now abandoned. The entire contents of which above-referenced application is herein incorporated by reference.

BACKGROUND OF THE INVENTION

This invention relates to a method and apparatus for growing biomass particles, particularly microcarrierbound cells. More particularly, this invention relates to an improved particle settling chamber which is used in conjunction with an agitated suspension culture vessel, also known as a perfusion culture bioreactor.

In recent years there has been rapid growth in the development of various methods for the culturing of cells in suspension with the goal of attaining high cell densities. Batch culture systems, which utilized a fixed amount of nutrient medium, have been replaced with continuous or semi-continuous basis as described, for example in U.S. Pat. No. 4,166,768. In such continuous systems spent culture medium is withdrawn through a filter, which is immersed in the agitated culture medium. This filter is inevitably subject to clogging, which limits the time the continuous system can be operated.

In U.S. Pat. No. 4,335,215, there is disclosed a modified continuous culture system which is said to improve the growth of microcarrier-bound cells. In this modified system, the immersed filter of the prior systems is replaced with a settling chamber which is external to the main culture vessel. During operation, culture medium is withdrawn from the main agitated culture vessel through a narrow tube into the bottom of the settling chamber then out through the top of the chamber, since there is no agitation in the settling chamber, the microcarrier beads slowly settle by gravity to the bottom of the settling chamber and back through the narrow tube into the main agitated culture vessel, when the microcarrier beads contact each other along the sloping surfaces of the settling chamber and in the narrow tube, this is said to promote aggregation of beads and bead-to-bead cell growth.

There are several problems associated with the above-described systems. The bottom opening of the settling chamber and the narrow tube which connects the settling chamber to the main vessel have a relatively small diameter. The diameter of the connecting tube is generally dictated by the size of the port available on the main vessel. In these narrow areas the upward fluid velocity of medium is often significantly higher than the settling velocity of the beads, causing the beads to become clogged. In fact, this problem is partially addressed by the patentee who suggests reversal of the pumps to ensure free movement of the beads in the narrower portions.

Another problem associated with this design concerns sterilization of the system. Since the settling chamber is external to the main reactor, the chamber and all connections are difficult to sterilize and to maintain sterility during operation.

Citation of documents herein is not intended as an admission that any of the documents cited herein is pertinent prior art, or an admission that the cited documents is considered material to the patentability of any of the claims of the present application. All statements as to the date or representation as to the contents of these documents is based on the information available to the applicant and does not constitute any admission as to the correctness of the dates or contents of these documents.

SUMMARY OF THE INVENTION

The present invention provides an improved method and apparatus for growing biomass particles, particularly microcarrier-bound cells, in an agitated suspension culture vessel in which fresh culture medium is added and spent culture medium is withdrawn continuously and/or semi-continuously. The improvement comprises withdrawing the spent culture medium is withdrawn continuously or semi-continuously. The improvement comprises withdrawing the spent culture medium through a particle settling chamber located within the vessel and at least partially immersed in the agitated culture medium therewithin. The particle settling chamber comprises a hollow container with a bottom opening through which biomass particles, such as microcarrier-bound cells, settle by gravity back into the agitated culture medium and a top opening through which particle-free spent culture medium is withdrawn from the vessel. The settling chamber is configured such that the fluid velocity of culture medium entering the settling chamber through the bottom opening is significantly less than the biomass particle settling velocity. That is, the uprising velocity of culture medium within the lower part of the settling chamber must be less than the downward biomass particle settling velocity.

BRIEF DESCRIPTION OF THE DRAWINGS

FIG. 4b depicts a top sectional view taken along line 4b—4b of the culture vessel illustrated in FIG. 4a.

FIG. 5b is a perspective view of the bottom of the settling tube 55 as seen along line 5b—5b of FIG. 5a, and FIG. 5c is a perspective view of impeller 56.

DETAILED DESCRIPTION OF THE INVENTION

The improved method and apparatus of the present invention can be utilized in conjunction with any perfusion bioreactor or continuous cell culture system. Such systems are designed to achieve efficient cell growth by maintaining optimum growth conditions during the entire process. These systems are especially suited for culturing cells as an agitated suspension of biomass particles, particularly microcarrier-bound cells.

The term biomass particles is intended to embrace any cells, including plant, animal bacteria, insect, fungus, yeast, or hybridoma cells, which can be grown in an agitated suspension culture medium and which have sufficient mass to settle by gravity with a reasonable settling velocity in non-agitated medium. In particular, biomass particles include microcarrier-bound cells. The term microcarrier-bound cells in intended to embrace anchorage-dependent cells, which are typically mammalian cells such as C127, COS or CHO cells, bound to microcarrier particles such as glass, polystyrene, gelatin, agarose or cellulose beads, and anchorage independent cells, such as hybridoma cells, bound within the matrices of porous microcarrier particles, for example particles comprising a collagen or gelatin sponge matrix. The term biomass particles is also intended to embrace all other cell systems which behave similar to microcarrier systems including, for example, cells encapsulated in beads and cells which collect as particles of sufficient mass that they will settle by gravity similar to microcarrier systems.

Figure 1:
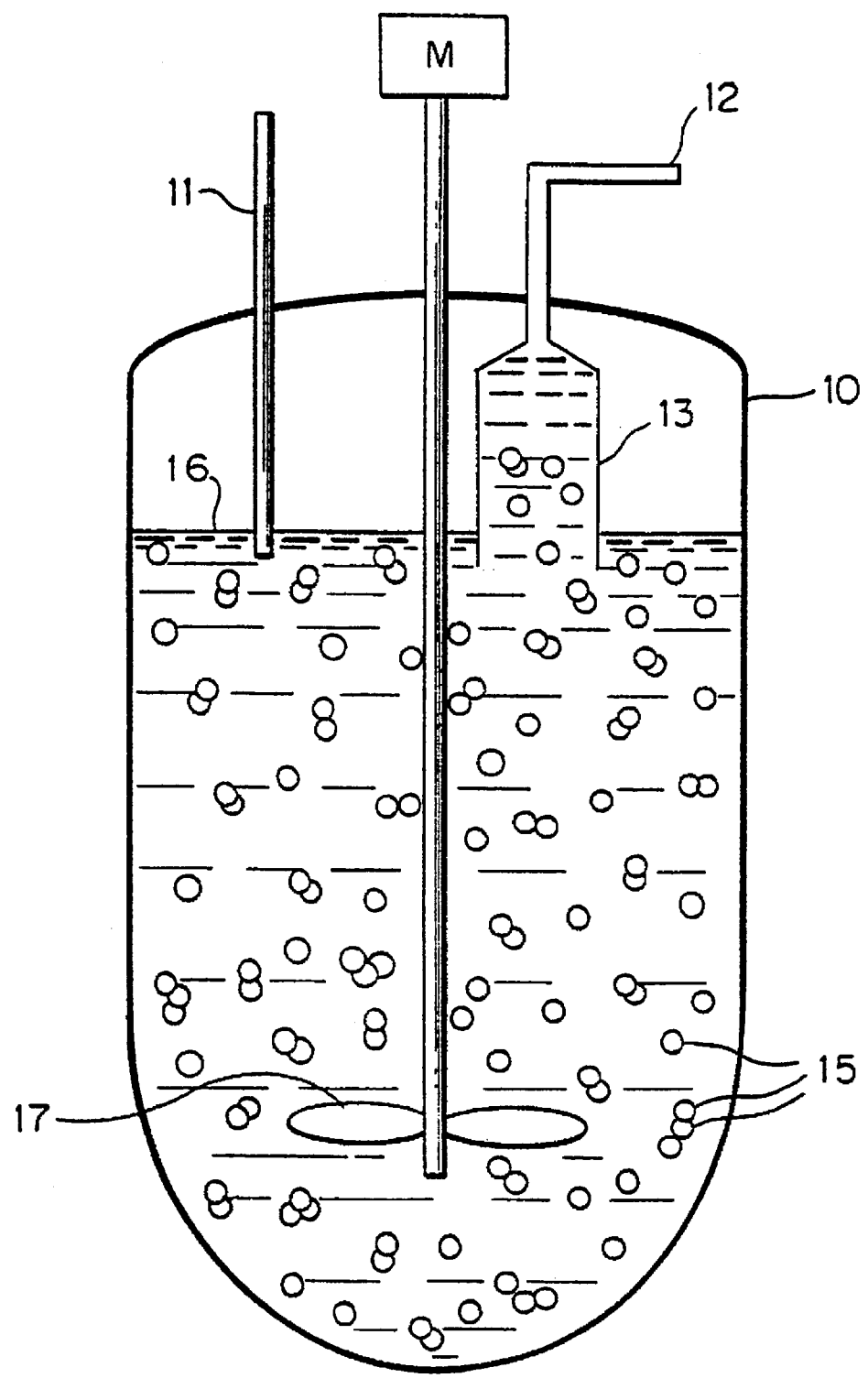
FIG. 1 depicts a cross-sectional view of an agitated suspension culture vessel with the improved particle settling chamber of the present invention.

A typical cell culture perfusion system may be described with reference to FIG. 1. In such a system, biomass particles 15 (enlarged for illustration purposes), which are typically microcarrier-bound cells, are suspended in culture medium 16, which is gently stirred by agitator 17 and maintained at a fixed level within bioreactor or culture vessel 10. Throughout the cell growth process, optimum growth conditions are maintained by supplying oxygen, carbon dioxide, pH-controlling substances, etc. as necessary. In addition, fresh culture medium is continuously or semi-continuously added to the vessel through inlet line 11, while at the same time an equal quantity of spent culture medium is withdrawn from the vessel through outlet line 12. If desired, some of the spent culture medium may be recycled back to the vessel. The addition and withdrawl of culture medium through lines 11 and 12 is generally controlled by peristaltic pumps, although any means of regulating a pressure differential, flow rate or liquid level may be employed.

Figure 2A:
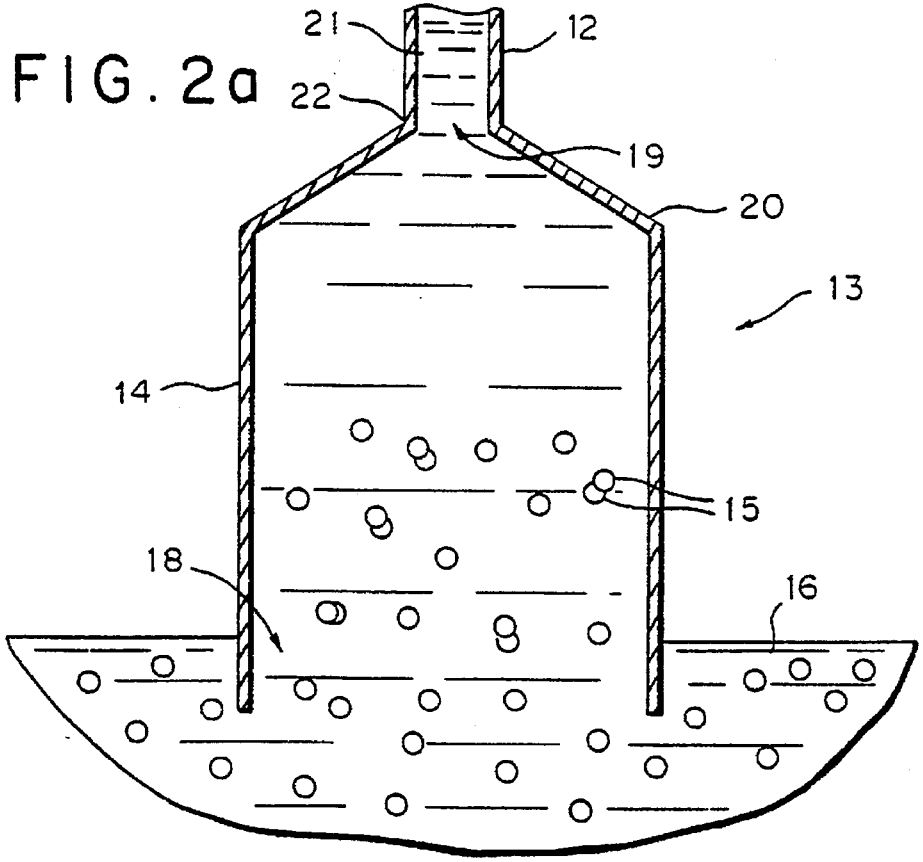
FIG. 2a depicts an enlarged cross-sectional view of the particle settling chamber shown in FIG. 1.

The improvement of the present invention resides in the use of the particle settling chamber 13, which is disposed within culture vessel 10 and partially immersed in culture medium 16. This settling chamber is more clearly depicted in FIG. 2a and generally comprises a hollow container 14, preferably of cylindrical shape, with a bottom opening 18 through which the biomass particles 15 settle by gravity back into the agitated culture medium 16 and a top opening 19 through which spent culture medium 21 is withdrawn from the culture vessel via outlet line 12.

Figure 2B:
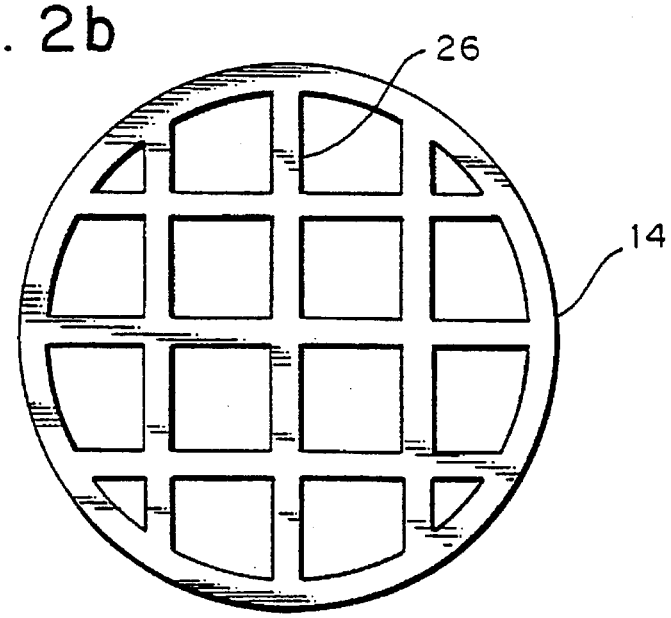
FIG. 2b depicts a bottom view of the particle settling chamber of FIG. 2a with an optional grid installed to reduce agitation.

The settling chamber is configured such that the fluid velocity of culture medium entering upwardly through the bottom opening is less, and preferably significantly less, than the biomass particle settling velocity. In the embodiment shown in FIGS. 1 and 2, the uppermost portion 20 of settling chamber 13 has a cone or inverted funnel shape, wherein the narrow portion 22 of the cone or inverted funnel defines the top opening 19. In this embodiment the settling chamber 13 is closed to the atmosphere with the culture vessel 10 and the top opening 19 communicates exclusively to a point outside the culture vessel via outlet line 12. It may be advantageous to fit a grid 26, as shown in FIG. 2b, into the bottom opening of the settling chamber, to serve as a means to reduce or prevent agitation within the chamber that might be caused by the agitated culture medium in the vessel.

Figure 3A:
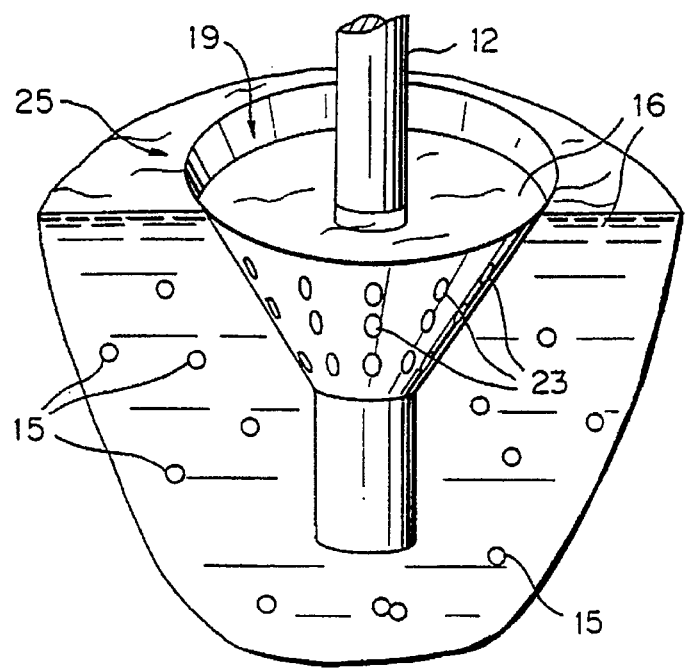
FIGS. 3a and 3b depict alternative configurations of particle settling chambers within the present invention.
Figure 3B:
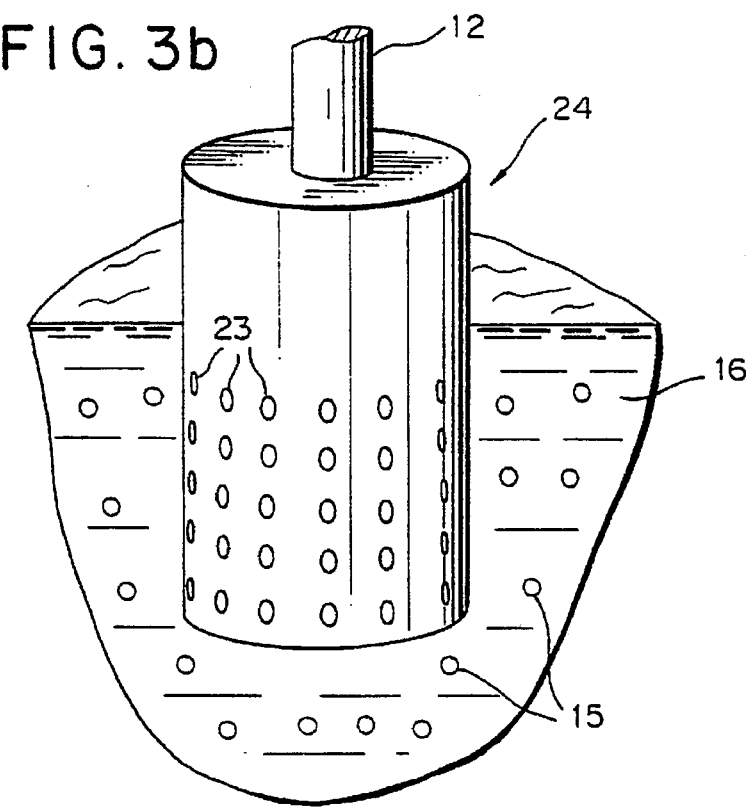

It will be readily apparent that the settling chamber may take a variety of other equally suitable configurations and, thus, the present invention is not restricted to the specific embodiment described above. For example, two other embodiments are illustrated in FIGS. 3a and 3b. Settling chamber 24, shown in FIG. 3b, is similar to the one previously described in that it has an essentially cylindrical shape and is not open to the atmosphere within the culture vessel. However, it has a plurality of holes 23 disposed along the sides such that these holes are below the surface of the culture medium 16 during use. These holes are sized and located so as to allow culture medium and biomass particles to enter the settling chamber, while avoiding significant agitation therewithin and minimizing the entry of biomass particles into outlet line 12. Grid 26 may be used in combination with holes 23.

Alternative settling chamber 25, shown in FIG. 3a, has a rather different configuration. This embodiment is funnel shaped with a relatively wide top opening 19 that is open to the atmosphere within the culture vessel. There are a plurality of hole 23 disposed along the sides of the chamber below the surface of the culture medium 16 so as to allow culture medium and biomass particles to enter the chamber, but sized so as to minimize agitation therewithin.

In this embodiment, outlet line 12 is a dip tube which extends through the top opening of the chamber into the culture medium therewithin.

Figure 4A:
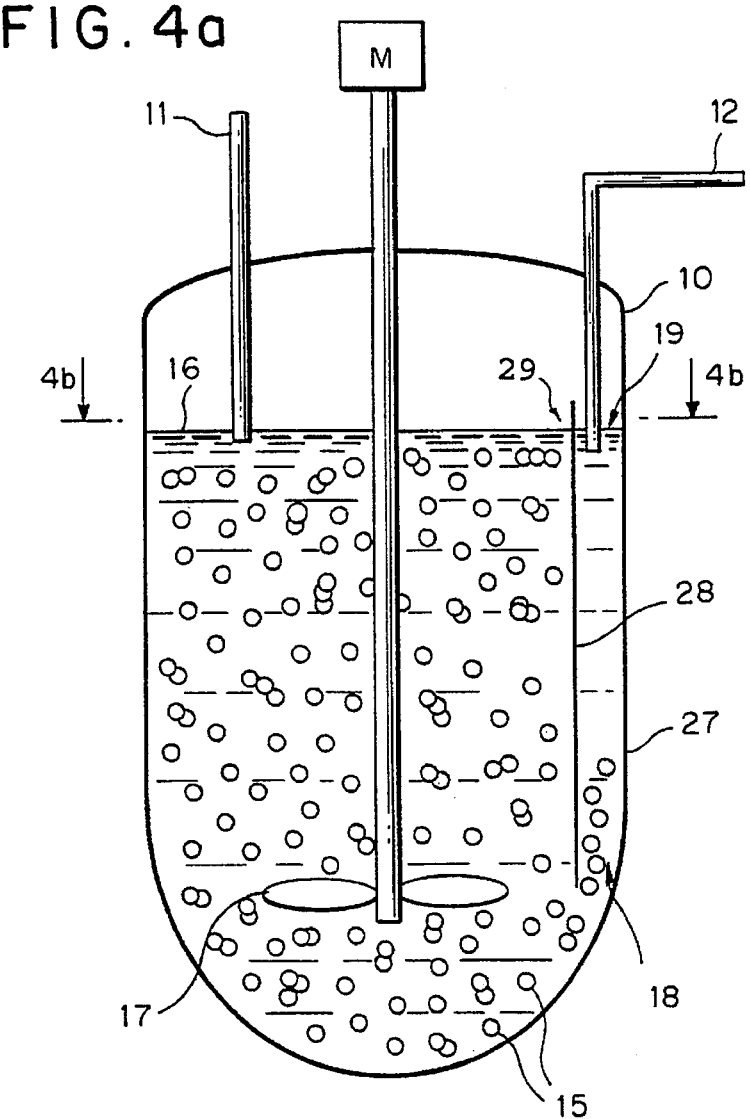
FIG. 4a depicts a cross-sectional view of an agitated suspension culture vessel with a fourth embodiment of the improved particle settling chamber of the present invention.
Figure 4B:
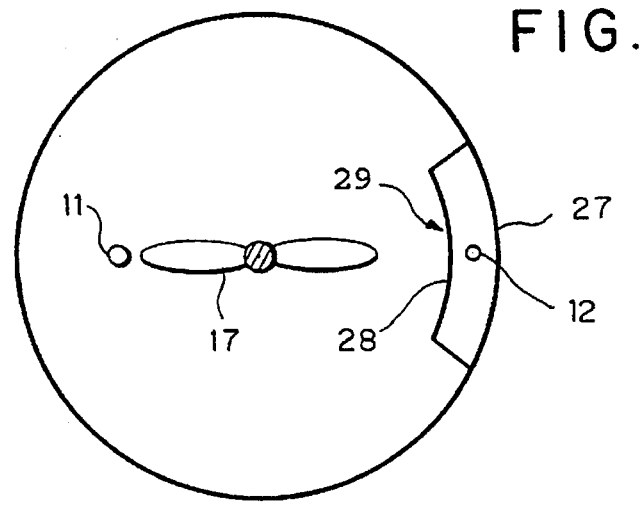

A fourth embodiment of the present invention is illustrated in FIGS. 4a and 4b. As shown in FIG. 4a, the culture vessel 10, inlet line 11, outlet line 12, biomass particles 15, culture medium 16 and agitator 17 are similar to the corresponding elements shown in FIG. 1. However, in this embodiment the settling chamber 29 comprises a hollow container in which one container wall 27 is formed by a portion of the culture vessel wall piece 28 which extends inwardly from the culture vessel wall and abuts the culture vessel wall along two separate and approximately vertical lines. As shown in FIG. 4a, wall piece 28 extends above the level of the culture medium 16 and the top opening 19 is open to the atmosphere within the culture vessel. Culture medium is withdrawn through outlet line 12, which in this case is a dip tube which passes through opening 19 into the culture medium within the settling chamber. Any biomass particles 15 which enter the settling chamber will settle by gravity through bottom opening 18 into the agitated culture medium.

As will be apparent, settling chamber 29 may optionally contain a plurality of holes (not shown) disposed along wall piece 28, similar to the embodiments shown in FIG. 3, in order to allow culture medium and biomass particles to enter the chamber. Naturally, of course, any such holes should be located far enough away form outlet line 12 so as to prevent withdrawal of biomass particles from the culture vessel and should be sized so as to minimize agitation within the settling chamber. It will also be apparent that settling chamber 29 may optionally be closed to the atmosphere within the culture vessel by placing a cap (not shown) over it. As a further option, wall piece 28 may be a continuous annular wall (not shown) concentric with the culture vessel wall so that the space between the culture vessel wall and the annular wall serves as the settling chamber, while the space inside the annular wall contains the agitated culture medium.

The apparatus of the present invention may be constructed of any sterilizable material which is suitable for bioreactors, including stainless steel, glass, ceramic, polymers, etc. Since the settling chamber may be disposed at any suitable location within the culture vessel, it can be sterilized concurrently with the culture vessel. The use of a settling chamber in accordance with the present invention avoids the necessity of employing a filter to prevent biomass particles cells from being withdrawn along with the spent culture medium, thus avoiding the possibility of a filter clog which would necessitate the premature shut-down of the process.

The present invention is further described, but limited to, the following example.

EXAMPLE I

Method and Apparatus for Growing Microcarrier Attached Cells in a Perfusion Mode and Comparison to Conventional Spin Filter Apparatus and Method An apparatus and method of the present invention was tested and found to compared with an existing conventional spin filter.

In summary, a bioreactor according to the present invention has achieved substantially about 100% of cell retention for microcarriers and an overall cell retention rate of about 95%. This new device does not have the problem of clogging during a prolonged operation, as frequently happens for spin filter type bioreactors. When this occurs, the overall retention rates of a spin filter may drop to less than 50%. The effective bioreactor working volume is higher when the present invention apparatus is used. The higher retention rate the higher concentration and number of cells in a bioreactor, such that the resulting products from the bioreactor are provided more efficiently in greater yields and purity relative to conventional bioreactors.

Materials and Methods

A chinese hamster ovary (CHO) cell line was used to grow in the bioreactor. A vial of CHO cells were thawed, then subcultured in suspension through a 250 ml spin flask, a 3 L spin flask, and 15 L spin flask. The medium was a 1 to 1 mixture of Iscove's Modified Dulbecco's medium (IMDM) and Ham's F12 modified medium. For the growth medium, 3% of fetal bovine serum (FBS) were added while the production medium contained 1% FBS.

Conventional Spin Filter Bioreactor Set Up

Figure 5:
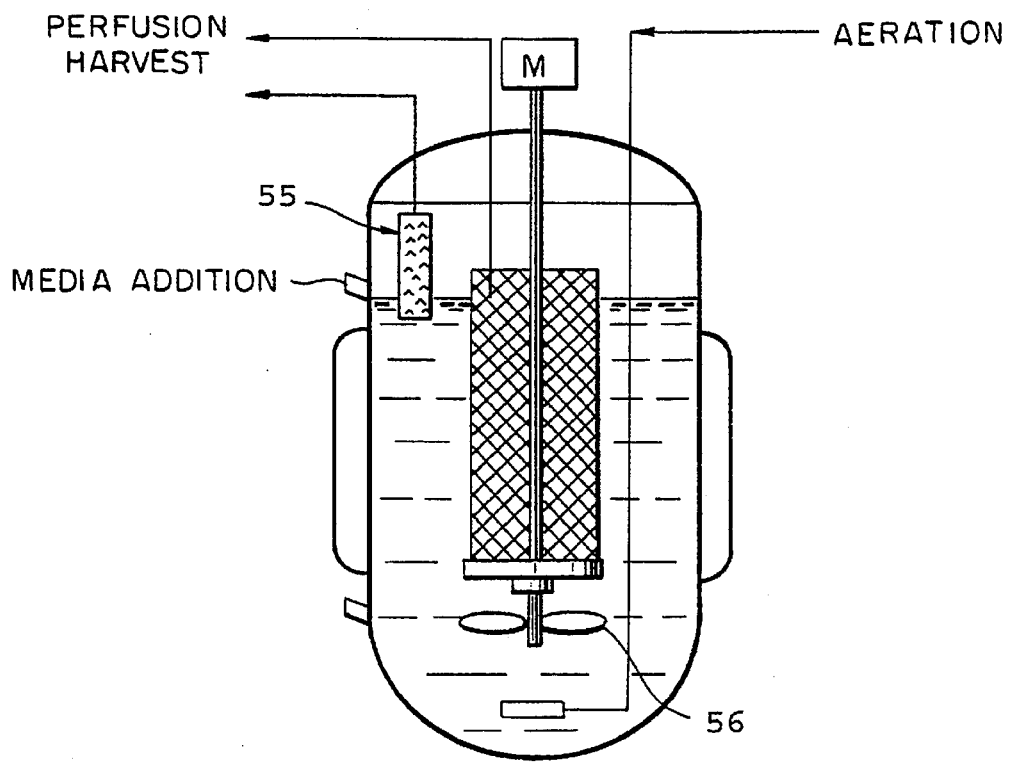
FIGS. 5, 5a, 5b and 5c depict a bioreactor used in example 1 wherein 5a is an elevational view of settling tube 55.
Figure 5A:
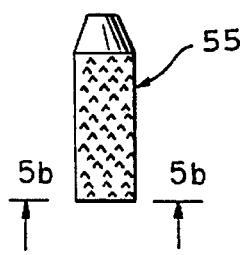
Figure 5B:
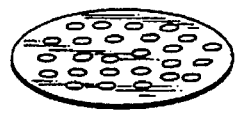
Figure 5C:

After the cell density reached $10^6$/ml, cell suspension from a 15 L spin flask was inoculated into the 80 L agitated bioreactor (Applikon, Netherlands), illustrated in FIG. 5 and described herein. The bioreactor was equipped with a conventional spin filter (75 micron pore size), a hydrofoil impeller, and a sintered steel sparger (15 micron pore size). The spin filter and the hydrofoil impeller were attached on the top-driven agitation shaft. For the perfusion operation, fresh medium was fed into the bioreactor and the spent medium was removed from the inside of the spin filter through a harvest tube ending at the level of 50 L working volume. A high pumping speed was used on the harvest line to ensure the level would not be over 50 L. The perfusion is then controlled by the medium feeding rate. A perforated stainless steel sheet (Stork Veco Int'l, Type 100 B, 150 micron pore size) was wrapped on the top of the spin filter to exclude microcarriers from entering the spin filter when the filter was clogged and medium overflow the filter rim.

Bioreactor of the Present Invention Set Up

A bioreactor according to the present invention was also assembled for a comparison with the use of a conventional spin filter and a particle settling chamber in a bioreactor according to the present invention. As illustrated in FIG. 1, the particle settling chamber is composed of a stainless steel cylinder (1 cm inside diameter), a plastic bottom plate with numerous holes (0.5 mm pore size), and four plastic sheets inside of the cylinder to minimize the liquid turbulence. For this protocol device, a filter housing (Paul, P/N: VSGTL1G723L) was used as the cylinder. It was tri-clamped to a second harvest tube on the top plate of the bioreactor. The holes on the bottom plate allowed medium to enter the cylinder and microcarriers to settle back into the bulk medium of the bioreactor. The harvest flowrates were set to be identical to the medium feed flowrate. The feed and harvest pump were set at 750 L/day flow rates but were activated by the controller for only a small percent of time in the 1 minute cycle. (For a 50 L perfusion rate, the pump activation percentage would be 50÷750=6.7%, i.e. 4 sec. per minutes.)

For the 50 L working volume of medium in the 80 L (total volume) bioreactor, a total of 250 g of Cytodex-3 was used to achieve the final microcarrier concentration at 5 g/L. After inoculation, the agitation of the bioreactor was turned on for 10 minutes at 10 rpm and then was turned off for 20 minutes to promote the attachment of cells on microcarriers. This agitation pattern was repeated several times before the agitation was maintained at 25 rpm. At Day 5, the bioreactor was put on the perfusion of growth media at 0.5 working volume per day, i.e. around 25 L of medium per day. The harvest was through the spin filter.

The perfusion rates and the agitation were adjusted several times during the run to exam the effects on production, retention rates, etc. On Day 9, the perfusion rate was increased to 0.75 volume/day. On Day 10, the agitation rate was increased to 50 rpm. On Day 11, the perfusion rate was increased to 1 volume per day. On Day 12, the perfusion was increased to 1.5 volume per day with 25 L/day of growth medium (3% FBS) and 50 L/day of production medium (1% FBS). On Day 12, the perfusion was done with 1.5 volume of production medium per day. On Day 17, the agitation rate was increased from 50 rpm to 75 rpm to improve oxygen transfer capability and to decrease foaming. On Day 19 the harvest of perfusion operation was switched from the spin filter to the patent device, an internal settling tube, to compare the retention rate. On Day 28, the perfusion rate was increased to 2 volumes per day and the perfusion was switched back to the spin filter. On Day 30, the run was terminated.

RESULTS AND DISCUSSIONS

The retention rates of microcarriers and attached cells remained at a constant value of 100% throughout the 30 day run. Table 1 summarizes the cultivation time, perfusion rates, cell concentrations in the bioreactors and in the harvest and retention rates. The overall retention rates were calculated by dividing the cell concentration of the harvest with the sum of attached and unattached cell concentrations in the bioreactor. Using the worst case of Day 23 as an example, the overall retention rate of the settling tube on that day was $6.3 \times 10^3/(9.8 \times 10^3 + 1.27 \times 10^7) = 95.4\%$ for the perfusion of the present invention.

Before the switch of perfusion from the spin filter to the settling tube on Day 19, the bioreactor working volume had increased to 10% higher, which was an indication that clogging of the spin filter had already occurred. Since the medium level in the bioreactor was higher than the rim of the spin filter, the medium overflowed the filter. The perforated screen on the top of the spin filter could prevent microcarriers, but not suspension cells, from entering the harvest zone. The clogging would become worse and the retention rates of suspension cells would have decreased further, unless the switch was made over of harvest mode on Day 19 to the use of the settling tube bioreactor of the present invention.

After the settling tube was used, the retention rates of microcarriers and attached cells remained at 100%. The total retention rate is superior with an overall retention rate of over 95% using a settling tube bioreactor of the present invention.

Note that the settling tube device had comparable retention rates with the spin filter, but the later was subject to filter clogging during prolonged operation. Another benefit of the present invention is that the settle tube takes a much smaller volume than the spin filter. Consequently, the real working volume in the bioreactor is higher when the settling tube is used. Recent studies also show that the diffusion of oxygen and nutrients through the spin filter is very low, which lead to significant cell death inside the spin filter. In contrast, a settling tube bioreactor of the present invention does not suffer from such problems involving sufficiency of oxygen or nutrient supply. The settling tube design, with much larger holes on the plate than the spin filter design, clearly has advantages in this regard.

Note that the pump rate can be decreased for an even higher total retention rate of the settling tube. For example, the pump flow rates can be set at 150 L/day. The 50 L/day perfusion can be achieved with 33% activation of pumps in the one minutes cycle. The lower pump rates would lead to a higher retention rate. More dividers can be inserted into the settling tube to further minimize liquid turbulence and to maximize the retention rate of suspension cells.

Accordingly, an apparatus and method according to the present invention is shown to have comparable or superior results in cell retention rates and has much superior bioreactor working volume and substantially no clogging during prolonged operation and a higher perfusion rate.

A bioreactor of the present invention is also expected to have superior cell retention rates and growth and production rates over conventional bioreactors for long term growth, e.g. of more than 10, 20, 30, 40, 50, 60, 70, 80, 90 or 100 days or more than 1, 2, 3, 4, 5, 6, 7, 8, 9, 10, 11 or 12 months.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

TABLE 1

THE PERFUSION RUN OF CHO/CYTODEX-3

| CULTIVATION HOUR | CULTIVATION DAY | PERFUSION RATE (L/O) | BIOREACTOR SUSPENSION CELL/ml | BIOREACTOR ATTACHED CELL/ml | BIOREACTOR TOTAL CELL/ml | HARVEST TOTAL CELL/ml | TOTAL RETENTION RATE % |
|---|---|---|---|---|---|---|---|
| 0 | 0 | 0 | N/A | N/A | 1.35E + 06 | N/A | N/A |
| 23 | 1 | 0 | N/A | N/A | 4.59E + 05 | N/A | N/A |
| 46 | 2 | 0 | N/A | N/A | 2.73E + 05 | N/A | N/A |
| 107 | 4 | 0 | N/A | N/A | 1.66E + 06 | N/A | N/A |
| 118 | 5 | 24 | N/A | N/A | 2.02E + 06 | 3.00E + 04 | 99% |
| 142 | 6 | 23 | N/A | N/A | 3.00E + 06 | 6.00E + 03 | 100% |
| 166 | 7 | 24 | 1.01E + 06 | 6.46E + 06 | 6.48E + 06 | 3.60E + 04 | 99% |
| 191 | 8 | 25 | 9.44E + 05 | 6.86E + 06 | 7.79E + 06 | 7.60E + 04 | 99% |
| 215 | 9 | 38 | 1.14E + 06 | 1.33E + 07 | 1.44E + 07 | 7.60E + 04 | 99% |
| 246 | 10 | 38 | 1.13E + 06 | 1.26E + 07 | 1.37E + 07 | 1.02E + 05 | 99% |
| 268 | 11 | 50 | 8.40E + 05 | 1.93E + 07 | 2.01E + 07 | 8.00E + 04 | 100% |
| 287 | 12 | 75 | 1.41E + 06 | 2.16E + 07 | 2.30E + 07 | 7.40E + 04 | 100% |
| 336 | 14 | 75 | 3.12E + 05 | 1.40E + 73 | 1.40E + 73 | 2.14E + 05 | 100% |
| 382 | 16 | 75 | 1.80E + 06 | 1.14E + 07 | 1.32E + 07 | 2.66E + 05 | 98% |
| 405 | 17 | 75 | 2.10E + 06 | 1.08E + 07 | 1.29E + 07 | 2.69E + 05 | 98% |
| 443 | 18 | 75 | 1.47E + 06 | 9.13E + 06 | 1.06E + 07 | 3.53E + 05 | 97% |
| 460 | 19 | 75 | 2.16E + 06 | 1.33E + 07 | 1.55E + 07 | 4.04E + 05 | 97% |
| 478 | 20 | 75 | 1.43E + 06 | 1.92E + 07 | 2.06E + 07 | 7.32E + 05 | 96% |
| 506 | 21 | 75 | 1.84E + 06 | 1.40E + 07 | 1.58E + 07 | 5.16E + 05 | 97% |
| 527 | 22 | 75 | 1.42E + 06 | 1.36E + 07 | 1.50E + 07 | 6.10E + 06 | 96% |
| 556 | 23 | 75 | 9.82E + 05 | 1.27E + 07 | 1.37E + 07 | 6.30E + 05 | 95% |
| 598 | 25 | 75 | 1.46E + 06 | 1.37E + 07 | 1.52E + 07 | 5.60E + 06 | 96% |
| 625 | 26 | 75 | 1.51E + 06 | 1.21E + 07 | 1.36E + 07 | 6.32E + 06 | 95% |
| 669 | 28 | 100 | 9.72E + 05 | 1.39E + 07 | 1.49E + 07 | 1.72E + 05 | 99% |
| 696 | 29 | 100 | 1.56E + 06 | 1.05E + 07 | 1.21E + 07 | 1.70E + 05 | 99% |

What is claimed:

1. A method for growing biomass particles in an agitated suspension culture vessel, comprising concurrently
    (A) adding fresh culture medium to an agitated suspension culture vessel containing biomass particles; and (B) withdrawing spent culture medium from said agitated suspension culture vessel containing biomass particles through a side perforated particle settling chamber which is at least partially immersed in an agitated culture medium within said vessel containing biomass particles, wherein (i) said particle settling chamber comprises a hollow container with a bottom opening through which said biomass particles settle by gravity back into the agitated culture medium and a top opening through which the spent culture medium is withdrawn from the vessel;

(ii) said chamber is configured such that a fluid velocity of the culture medium entering said container through said bottom opening is significantly less than a settling velocity of the biomass particles; and (iii) said hollow container has a plurality of holes disposed along the sides thereof, said holes being sized and located so as to allow culture medium and biomass particles to enter said container while avoiding significant agitation therewithin and minimizing withdrawal of biomass particles through the top opening thereof.

2. The method of claim 1, wherein said hollow container is (a) closed to the atmosphere within said vessel;

(b) said bottom opening being significantly larger in cross-sectional area than said top opening; and (c) said top opening communicates exclusively outside said vessel.

3. The method of claim 2, wherein said hollow container has an essentially cylindrical shape.

4. The method of claim 2, wherein said hollow container or an uppermost portion of said hollow container has a cone or inverted funnel shape, wherein the narrow portion of said cone or inverted funnel shape defines said top opening.

5. The method of claim 1, wherein said top opening is open to the atmosphere within said vessel and the spent culture medium is withdrawn from said vessel through a dip tube inserted through said top opening partially into said hollow container so as to contact the culture medium therewithin.

6. The method of claim 5, wherein said hollow container has one wall which is formed by a portion of the wall of said culture vessel and another wall which is formed by a wall piece that extends inwardly from said culture vessel wall portion and abuts the culture vessel wall portion along two separate and approximately vertical lines.

7. The method of claim 1, wherein said biomass particles comprise microcarrier-bound cells.

8. An apparatus for growing biomass particles, comprising an agitated suspension culture vessel, a particle settling chamber disposed within said vessel such that it will be at least partially immersed in agitated culture medium during use, wherein (i) said particle settling chamber comprises a hollow container with (1) a bottom opening through which said biomass particles settle by gravity back into an agitated culture medium and (2) a top opening through which spent culture medium is withdrawn from the vessel;

(ii) said chamber is configured such that a fluid velocity of the culture medium entering said container through said bottom opening is significantly less than a settling velocity of the biomass particles; and (iii) said hollow container has a plurality of holes along the sides thereof, said holes being sized and located so as to allow the culture medium and biomass particles to enter said container while avoiding significant agitation therewithin and minimizing withdrawal of biomass particles through the top opening thereof.

9. The apparatus of claim 8, wherein said top opening communicates solely outside said vessel and said bottom opening is significantly larger than said top opening, wherein during use said hollow container is closed to the atmosphere within said vessel.

10. The apparatus of claim 9, wherein said hollow container has an essentially cylindrical shape.

11. The apparatus of claim 9, wherein said hollow container or an uppermost portion of said hollow container has a cone or inverted funnel shape, wherein the narrow portion of said cone or inverted funnel shape defines said top opening.

12. The apparatus of claim 8, further comprising a dip tube which extends from a point outside said vessel through said top opening partially into said hollow container, such that during use said dip tube contacts the culture medium within said hollow container, wherein said top opening is larger in cross-sectional area than said dip tube.

13. The apparatus of claim 12, wherein said hollow container has one wall which is formed by a portion of the wall of said culture vessel and another wall which is formed by a wall piece that extends inwardly from said culture vessel wall portion and abuts the culture vessel wall portion along two separate and approximately vertical lines.

14. An apparatus according to claim 8, wherein said hollow container comprises a grid located at or near the bottom opening, said grid reducing or preventing agitation within said hollow container.

15. An apparatus according to claim 14, wherein said grid is configured so as to readily allow biomass particles to pass through during use.

* * * * *